(12) United States Patent
Stein et al.

(10) Patent No.: US 6,264,959 B1
(45) Date of Patent: Jul. 24, 2001

(54) ULTRASONIC CONTRAST AGENTS, PROCESS FOR THEIR PREPARATION AND THEIR USE AS A DIAGNOSTIC AND THERAPEUTIC AGENT

(75) Inventors: Michael Stein; Dieter Heldmann; Thomas Fritzsch; Joachim Siegert; Georg Roessling, all of Berlin (DE)

(73) Assignee: Schering Aktiengesellschaft (DE)

( * ) Notice: Subject to any disclaimer, the term of this patent is extended or adjusted under 35 U.S.C. 154(b) by 0 days.

(21) Appl. No.: 07/536,373

(22) Filed: Jun. 11, 1990

Related U.S. Application Data

(63) Continuation of application No. 07/305,820, filed on Feb. 3, 1989, now abandoned.

(30) Foreign Application Priority Data

Feb. 5, 1988 (DE) ................................. 38 03 971
Feb. 5, 1988 (DE) ................................. 38 03 972

(51) Int. Cl.$^7$ ........................................... A61K 9/00
(52) U.S. Cl. ................ 424/400; 424/9.5; 424/9.4; 424/498; 424/486; 424/2
(58) Field of Search ............... 514/821; 128/653 R; 424/2, 498, 497, 486; 536/46

(56) References Cited

U.S. PATENT DOCUMENTS

| | | | |
|---|---|---|---|
| 4,186,131 | * 1/1980 | Kreighbaum | 514/821 |
| 4,466,442 | * 8/1984 | Hilmann | 128/653 R |
| 4,518,588 | * 5/1985 | Szejtli | 536/46 |
| 4,774,958 | * 10/1988 | Feinstein | 424/2 |
| 4,808,399 | * 2/1989 | Rypacek | 424/2 |

FOREIGN PATENT DOCUMENTS

89/00069 * 1/1989 (DE).

OTHER PUBLICATIONS

J. Szejtli, Cyclodextrins and Their Inclusion Complexes, Budapest 1982, pp. 131–134.
Proceedings of the first International Symposium on Cyclodextrins, 1981, Recovery of Solvent Vapours from Gaseous Phase by Cyclodextrins Solutions pp. 525–529.
Derwent–Abstract 88–188752/27 (SU 1357410) (CA 108:206596t 1988).
Derwent–Abstract 87–089900/13 (JP 62039602).
Derwent–Abstract 87–018962/03 (JP 61277610 (CA 106:162392) p. 1987.

* cited by examiner

*Primary Examiner*—Thurman K. Page
*Assistant Examiner*—W. Benston
(74) *Attorney, Agent, or Firm*—Miller, White, Zelano & Branigan, P.C.

(57) ABSTRACT

The invention relates to ultrasonic contrast agents consisting of microparticles which consist of amyloses and synthetic biodegradable polymers and a gas and/or a fluid with a boiling point below 60° C., process for the preparation thereof and their use as diagnostic and therapeutic agents.

18 Claims, No Drawings

ULTRASONIC CONTRAST AGENTS, PROCESS FOR THEIR PREPARATION AND THEIR USE AS A DIAGNOSTIC AND THERAPEUTIC AGENT

This is a continuation of application Ser. No. 07/305,820 filed Feb. 3, 1989 Abnd. Mar. 13, 1990.

The invention relates to microparticles according to the specification, a process for their preparation and their use as a diagnostic and therapeutic agent.

It is known that cardial echo contrasts can be achieved through peripheral injection of solutions which contain fine gas bubbles (Roelandt J, Ultrasound Med Biol 8:471–492, 1982). These gas bubbles are obtained in physiologically compatible solutions, eg through shaking, other agitation or through the addition of carbon dioxide. However they are not standardized in terms of number and size and cannot be adequately reproduced. Also they are as a rule not stabilized so that their service life is short. Their average diameters are generally above the erythrocyte size so that it is not possible to obtain pulmonary capillary passages with subsequent contrasting of organs such as the left heart, liver, kidneys or spleen. Furthermore they are not suitable for quantifications since the ultrasonic echo which they produce is made up from several processes which cannot be separated from each other such as the formation of the bubbles, coalescence and dissolution. Thus it is not possible for example to obtain definite details on the transit times with the aid of these ultrasonic contrast agents by measuring the contrast path in the myocardium. This requires contrast agents whose dispersal bodies are not subject to their own kinetics.

In addition there are ultrasonic contrast agents in the form of particles (Ophir, Gobuty, McWhirt, Maklad, Ultrasonic Backscatter from Contrast-producing Collagen Microspheres, Ultrasonic Imaging 2:66–67, 1980). Furthermore solutions of a higher density are used as ultrasonic contrast agents (Ophir, McWhirt, Maklad, Aqueous Solutions as Potential Ultrasonic Contrast Agents, Ultrasonic Imaging 1:265–279, 1979 as well as Tyler, Ophir, Maklad, In-vivo Enhancement of Ultrasonic Image Luminance by Aqueous Solutions with High Speed of Sound, Ultrasonic Imaging 3:323–329, 1981). It is also known to use emulsions as ultrasonic contrast agents (Mattrey, Andre, Ultrasonic Enhancement of Myocardial Infarction with Perfluorcarbon Compounds in Dogs, Am J Cardiol 54:206–210, 1984).

It has been seen that overall the gas-free contrast agents only have a low efficiency. The gas-containing preparations have the disadvantage of only a slight in-vivo stability. Furthermore the size of the gas bubbles can generally not be standardized. As a rule adequate contrast effects are not possible in the arterial vessel system after a peripheral veinous injection.

In EP A2 123 235 and 0 122 624 ultrasonic contrast agents are described which contain small gas bubbles and which pass through the pulmonary capillaries producing the desired contrast effect.

EP A2 0 224 934 describes ultrasonic contrast agents in the form of gas-filled gelatine or albumin hollow bodies. However the disadvantage here is the use of foreign-body albumens or denatured albumens belonging to the body and thus the associated risk of allergy.

With none of the ultrasonic contrast agents known up until now is it possible to represent the organs with sufficient signal intensity through selective concentration after an i.v. dose. Quantifications are therefore not possible at the present time.

contrast agents on the basis of microparticles which in addition to a determinable and reproducable volume have a considerably longer service life that previously known, offer good comparability without allergic potential and can be concentrated intracellularly in RES and thus also in the liver or spleen.

This is achieved in accordance with the invention by micro particles which consist of amylose or a synthetic biodegradable polymer and a gas and/or a fluid with a boiling point below 60° C.

Polyesters of $\alpha$-, $\beta$-, $\gamma$- or $\epsilon$-hydroxy carbonic acids, polyalkyl-cyanoacrylates, polyamino acids, polyamides, polyacrylated saccharides or polyorthoesters are named as synthetic biodegradable polymers.

The following have proved particularly suitable:

Polylactic acid,

Poly-$\epsilon$-caprolacton,

Copolymers of lactic acid and glycol acid or $\epsilon$-caprolacton,

Polyhydroxybutyric acid,

Polyhydroxyvaleric acid,

Copolymers of hydroxybutyric and hydroxyvaleric acid,

Polymers of glutamic acid and/or lysine,

Polydioxanon,

Polymers or copolymers of amino acids and/or terephthalic acid, phthalic acid or sebacic acid, Polyacryldextran, Polyacryl starch, Polyacrylamide, Polyurethane, Polyester, Polyacetal, Polyaminotriazol or Polyalkylcyanoacrylate.

Starch or starch derivatives can also be contained in the microparticles. Amyloses have proved particularly suitable since these starch derivatives have excellent water solubility and the ability to form inclusion compounds.

Amyloses which are particularly suitable are the cyclodextrines and their derivatives, by way of example $\alpha$, $\beta$, and $\gamma$-cyclodextrin.

The microparticles contain gases and/or fluids with a boiling point below 60° in free or bonded form. The use of a gas-fluid mixture in the ultrasonic contrast agents is likewise possible.

Gases used can be for example air, nitrogen, inert gases, hydrogen, carbon dioxide, ammonia, oxygen, methane, ethane, propane, butane, ethylene or other hydrocarbons or their mixtures.

Preferred fluids which can be included are:

1,1-dichloroethylene, 2-methyl-2-butene, isopropyl chloride, 2-methyl-1,3-butadiene, 2-butyne, 2-methyl-1-butene, dibromodifluoromethane, furan, 3-methyl-1-butene, isopentane, diethylether, 3,3-dimethyl-1-butyne, dimethylaminoacetone,
propylene oxide,
N-ethylmethylamine,
bromomethane,
n-ethyldimethylamine,
methylene chloride,
pentane,
cyclopentane,
2,3-pentadiene,
cyclopentene or mixtures thereof.

The microparticles can also contain advantageously substances with low steam pressures and/or low boiling points, in particular ethereal oils.

It is particularly advantageous to coat the microparticles which consist of amylose with a coating substance. The microparticles can thereby be encased in oils, fats and/or surface-active substances and suspended in an aqueous medium.

It is particularly advantageous to encase the microparticles which consist of amylose in a matrix, more particularly of a polymer structure.

The physiological isotony can be set by the addition of osmotically active substances such as cooking salt, galactose, glucose, fructose.

An advantageous process for preparing the ultrasonic contrast agents according to the invention consists in dissolving a polymer or copolymer in one or more organic solvents which are not miscible with water, followed by the emulsification in water, possibly with the addition of a further solvent, and then filtering and if required drying the emulsion obtained.

A further process consists in dissolving a polymer or copolymer in one or more solvents which contain gas bubbles, after which it is precipitated or emulsified in water, if required with the addition of a further solvent or a further polymer, and then the suspension or emulsion which has been obtained is then filtered and if required dried. The freeze-drying process is also suitable as a finishing process.

The products obtained can advantageously be finely ground.

In the processes described, the solvents used can be for example furan, pentane, acetone, dioxen, ethyl acetate, xylol, methylene chloride, cyclohexane or hexane or solvent mixtures. Emulsifiers can also be added to the emulsion.

In a further variation of the manufacturing process instead of polymers monomers are used as the starting product from which the polymer is formed. With this process, a monomer is dissolved in one or more organic solvents and then emulsified in 5–30 parts water or 0.01–0.1 N hydrochloric acid, if required with the addition of emulsifiers or buffer substances at a temperature below the boiling point of the organic solvent, after which a 0.2%–20% aqueous solution of a second monomer or if required the solution of a substance increasing the pH-value is added to this emulsion and dried if required.

In another method of operation a monomer is dissolved or dispersed in one or more fluids containing gas bubbles, if required with the addition of emulsifiers or buffer substances. If required a 0.2%–20% solution of a second monomer or a substance increasing the pH-value in dissolved or gaseous form is added to this solution or dispersion and dried if required.

By way of example, terephthaloyl- or sebacoylchloride or cyanacrylic acid ester is used as a first monomer, L-lysine as the second monomer and for example 2-methyl-1,3-butadiene, dioxan, methylene chloride, toluene or cyclohexane is used as the organic solvent.

According to a further process, the ultrasonic contrast agents are prepared by producing gas bubbles in a 0.5–10% aqueous solution or dispersion of a monomer which contains if required additives such as emulsifiers (0.01–5%) or quasi emulsifiers (0.1–5%), and then by adding a cross-linking substance and/or a reaction starter.

The ultrasonic contrast agents described above can be used for both diagnostic and therapeutic processes.

The application of the agents is for example by injection.

Details, e.g., dosages and procedures, etc., are in accordance with those used for analogous agents in ultrasound imaging, e.g., are described in the publications mentioned herein and, e.g., in U.S. Pat. No. 4,276,885, all of which are fully incorporated by reference.

The invention will be explained by the following examples:

EXAMPLE 1

500 mg polylactide were dissolved in 4 ml furan and 0.6 ml cyclohexane and this solution was emulsified in 40 ml of a 0.1% solution of polyoxyethylene polyoxypropylene polymer with a molecular weight 12.0000 (Pluronic® F 127), with the temperature being kept beneath 15° C. during emulsifying. The temperature was then slowly raised to evaporate off the organic solvent. The resulting suspension was then freeze-dried.

EXAMPLE 2

300 mg α-cyanoacrylic acid butyl ester were dissolved in 1 ml furan and this solution was emulsified in 10 ml 0.1 N hydrochloric acid which contained 1% polyoxyethylene polyoxypropylene polymer with a molecular weight 12.000 (Pluronic® F 127), with the temperature being kept beneath 15° C. during emulsifying. At the end of polymerization the resulting suspension was freeze-dried.

EXAMPLE 3

200 mg α-cyanoacrylic acid butyl ester were dissolved in 0.4 ml isoprene and emulsified in 30 ml 0.01 N hydrochloric acid which contained 1% polyoxyethylene polyoxypropylene polymer with a molecular weight 8.350 (Pluronic® F 68), with the temperature being kept beneath 10° C. during emulsifying. At the end of the polymerization the suspension was neutralized with 0.1 N NaOH and isotonized with sodium chloride.

EXAMPLE 4

400 mg α-cyanoacrylic acid butyl ester were dissolved in 0.4 ml methylene chloride and emulsified in 60 ml 0.01 N hydrochloric acid which contained 1% polyoxyethylene polyoxypropylene polymer with a molecular weight 12.000 (Pluronic® F 127), with the temperature being kept beneath 10° C. during emulsifying. At the end of polymerization the suspension was neutralized with 0.1 N soda lye and isotonized with sodium chloride.

EXAMPLE 5

400 mg polycaprolactone were dissolved in 6 ml furan and 0.3 ml cyclohexane and emulsified in 60 ml 1% polyoxyethylene polyoxypropylene polymer with molecular weight 12.000 (Pluronic® F 127), with the temperature being kept beneath 15° C. The temperature was then slowly raised to evaporate off the organic solvent. The resulting suspension was then freeze-dried.

EXAMPLE 6

400 mg terephthalic acid dichloride were dissolved in 2 ml furan and then emulsified in 50 ml 3% sodium carbonate solution which contained 0.1% polyoxyethylene polyoxypropylene polymer with a molecular weight 12.000 (Pluronic® F 127). After the additon of 60 mg L-lysine, dissolved in 5 ml 0.1% Pluronic F 127, the micro capsules were centrifuged and washed several times with 0.1% Pluronic F 127 solution. Before use the suspension was isotonized with sodium chloride.

EXAMPLE 7

β-cyclodextrin-isopentane-inclusion compound:

100 ml saturated β-cyclodextrin solution (1.8%) were cooled to 10° C. and mixed with 3 ml isopentane. The resulting difficultly soluble complex was precipitated with constant stirring in the ultrasonic bath. The deposit was obtained in crystalline form through freeze-drying and filtration. Isopentane content according to GC calculation:0.25%

EXAMPLE 8

β-Cyclodextrin-2-methyl-2-butene-inclusion compound:

100 ml saturated P -cyclodextrin solution (1.8%) were cooled to 10° C. and mixed with 3 ml 2-methyl-2-butene. The resulting difficultly soluble complex was precipitated with constant stirring in the ultrasonic bath. The deposit was obtained in crystalline form through freeze-drying and filtering.

EXAMPLE 9

β-Cyclodextrin-2-methyl-1-butene-inclusion compound:

100 ml saturated β-cyclodextrin solution (1.8%) were cooled to 10° and mixed with 3 ml 2-methyl-1-butene. The resulting difficultly soluble complex was precipitated with constant stirring in the ultrasonic bath. The deposit was obtained in crystalline form through freeze-drying and filtering. 2-methyl-1-butene content according to GC calculation: 0.82%

EXAMPLE 10

β-cyclodextrin-isoprene-inclusion compound:

100 ml saturated β-cyclodextrin solution (1.8%) were cooled to 10° C. and mixed with 3 ml isoprene. The resulting difficultly soluble complex was precipitated with constant stirring in the ultrasonic bath. The deposit was obtained in crystalline form through freeze-drying and filtering. Isoprene content according to GC calculation: 1.0%

EXAMPLE 11

β-cyclodextrin-isopropylchloride-inclusion compound:

100 ml saturated )cyclodextrin solution (1.8%) were cooled to 10° C. and mixed with 3 ml isopropylchloride. The resulting difficultly soluble complex was precipitated with constant stirring in the ultrasonic bath. The deposit was obtained in crystalline form through freeze-drying and filtering. Isopropylchloride content according to GC calculation: 0.5%.

EXAMPLE 12

β-cyclodextrin-isopentane-inclusion compound:

100 ml saturatedβ-cyclodextrin solution (1.8%) were cooled to 10° C. and mixed with 3 ml isopentane. The resulting difficultly soluble complex was precipitated with constant stirring in the ultrasonic bath. The deposit was obtained in crystalline form through freeze-drying and filtering.

EXAMPLE 13

Xenon/β-cyclodextrin-inclusion compound:

100 ml saturated α-cyclodextrin solution (about 12%) were incubated under 7 atmospheres xenon for 7 days at room temperature in a 200 cc autoclave. The crystalline adduct could be sucked off, washed with cold water and dried via calcium chloride in the exsiccator.

EXAMPLE 14

Carbon dioxide/β-cyclodextrin-inclusion compound:

100 ml saturated α-cyclodextrin solution (about 12%) were incubated for 7 days at room temperature under 7 atmospheres carbon dioxide in a 20 cc autoclave. The crystalline adduct could be drawn off, washed with cold water and dried via calcium chloride in the exsiccator.

EXAMPLE 15

Isopentane/hydroxypropyl-β-cyclodextrin-inclusion compound:

15 ml 20% hydroxproply-β-cyclodextrin solution were mixed with 2 ml isopentane at 10° C., ultrasounded for 3 minutes in the ultrasonic bath and then incubated for 26 hours. The resulting complex remained in solution.

EXAMPLE 16

Isoprene/hydroxypropyl-β-cyclodextrin-inclusion compound:

15 ml 20% hydroxypropyl -β-cyclodextrin solution were mixed with 2 ml isoprene at 10° C., ultrasounded for 3 minutes in the ultrasonic bath and then incubated for 26 hours. The resulting complex remained partly in solution and precipitated partly as a white deposit.

EXAMPLE 17

Furan/hydroxypropyl-β-cyclodextrin-inclusion compound:

15 ml 20% hydroxypropyl-β-cyclodextrin solution were mixed with 2 ml furan at 10° C., ultrasounded for 3 minutes in the ultrasonic bath and then incubated for 26 hours. The resulting complex remained partly in solution and partly precipitated as a white deposit.

EXAMPLE 18

Isopentane/'-cyclodextrin-inclusion compound:

20 ml saturated (β-cyclodextrin solution were mixed with 1 ml isopentane and ultrasounded for 3 minutes in the ultrasonic bath. The resulting difficultly soluble complex was obtained through filtration and dried via calcium chloride.

EXAMPLE 19

Isoprene/α-cyclodextrin inclusion compound:

20 ml saturated α-CD-solution were mixed with 1 ml isoprene and ultrasounded for 3 minutes in the ultrasonic bath. The resulting difficultly soluble complex was obtained through filtration and dried via calcium chloride.

EXAMPLE 20

Furan/α-cyclodextrin-inclusion compound:

20 ml saturated α-cyclodextrin solution were mixed with 1 ml furan and ultrasounded for 3 minutes in the ultrasonic bath. The resulting difficultly soluble complex was obtained through filtration and dried via calcium chloride.

EXAMPLE 21

4 g eucalyptol was added dropwise to 100 ml saturated α-cyclodextrin-solution (5° C.) in an incubation chamber while being ultrasounded and was ultrasounded for a further 30 min. Thereafter the incubation chamber was shaken in a cooled, closed vessel for 48 hours. The resulting precipitate was filtered off, washed with cold ethanol, frozen in liquid nitrogen and freeze dried.

EXAMPLE 22

100 ml saturated β-cyclodextrin-solution was ultrasounded with 2 g Geraniol at 5° C. for 4 hours and thereafter incubated for 24 hours at 5° C. The resulting precipitate was filtered off, washed with cold ethanol, frozen in liquid nitrogen and freeze dried.

The following applies to Examples 7–22:

The crystalline deposit was absorbed after cleaning in a suitable aqueous medium, preferably physiological cooking salt, glucose or ringer solution and was then ready for injection.

What is claimed is:

1. An ultrasonic contrast agent comprising microparticles which are comprised of amyloses containing a gas and/or an organic fluid with a boiling point below 60° C., wherein said ultrasonic contrast agent is suitable for administration to a subject by injection.

2. An ultrasonic contrast agent according to claim 1, characterised in that the microparticles contain cyclodextrins or cyclodextrin derivatives as amylose.

3. An ultrasonic contrast agent according to claim 1, wherein the microparticles contain as an organic fluid with a boiling point below 60° C., a fluid from the class consisting of 1,1-dichloroethylene, 2-methyl-2-butene, isopropylchloride, 2-methyl-1,3-butadiene, 2-butyne, 2-methyl-1-butene, isopentane, diethylether, 3,3-dimethyl-1-butyne, dimethylamino acetone, propylene oxide, N-ethylmethylamine, bromomethane, N-ethyldimethyl amine, methylene chloride, pentane, cyclopentane, 2,3-pentadiene, cyclopentene and mixtures thereof.

4. An ultrasonic contrast agent according to claim 1 wherein the microparticles contain as a gas a member of the class consisting of air, nitrogen, oxygen, carbon dioxide, hydrogen, ammonia, ethylene, methane, ethane, propane butane and mixtures thereof.

5. An ultrasonic contrast agent according to claim 1, wherein the microparticles contain ethereal oils.

6. An ultrasonic contrast agent according to claim 1, wherein the microparticles comprising amyloses are coated with a hydrophobic coating substance which comprises oils, fats and/or surface-active substances and said microparticles are suspended in an aqueous medium.

7. An ultrasonic contrast agent according to claim 1, the microparticles comprising amyloses are covered by a polymer matrix.

8. An ultrasonic contrast agent according to claim 1 wherein the physiological isotony is set by the addition of osmotically active substances.

9. An ultrasonic contrast agent comprising solid microparticles which comprise amyloses containing a gas and/or organic fluid having a boiling point below 60° C., wherein said microparticles are of a size capable of passing through pulmonary capillaries and the organic fluids are selected from the group consisting the 1,1-dichloroethylene, 2-methyl-2-butene, isopropyl chloride, 2-methyl-1,3-butadiene, 2-butyne, 2-methyl-1-butyne, 2-methyl-1-butene, isopentane, diethylether, 3,3-dimethyl-1-butyne, dimethylamino acetone, propylene oxide, N-ethylmethylamine, bromomethane, N-ethyldimethylamine, methylene chloride, pentane, cyclopentane, 2,3-pentadiene, cyclopentene or mixtures thereof and said gases are selected from air, inert gases, nitrogen, oxygen, carbon dioxide, hydrogen, ammonia, ethylene, methane, ethane, propane and butane where said ultrasonic contrast agent is suitable for administration to a subject by injection.

10. A method of enhancing an ultrasonic image of a liquid which comprises administering an effective amount of an ultrasonic contrast agent in accordance with claim 1 to said liquid and obtaining an ultrasonic image of said liquid.

11. A method of enhancing the contrast of an ultrasonic image of a patient which comprises administering an effective amount of an ultrasonic contrast agent of claim 1 to a patient and obtaining an ultrasonic image of the patient where said ultrasonic contrast agent is present.

12. A method of enhancing the contrast of a cardial ultrasonic image which comprises injecting an effective amount of an ultrasonic contrast agent of claim 1 into the bloodstream of a patient and obtaining an ultrasonic image of the heart.

13. An ultrasonic contrast agent comprising microparticles comprised of amyloses and a gas and/or a fluid with a boiling point below 60° C. wherein said microparticles comprised of amyloses are produced within a "oil-in-water" emulsion.

14. Solid microparticles comprising amyloses containing a gas and/or a fluid with a boiling point below 60° C., wherein the microparticles are of a size capable of passing through pulmonary capillaries and are suitable for administration to a subject by injection.

15. Solid microparticles as in claim 14 with a fluid selected from the group consisting of 1,1-dichloroethylene, 2-methyl-2-butene, isopropylchloride, 2-methyl-1,3-butadiene, 2-butyne, 2-methyl-1-butene, isopentane, diethylether, 3,3-dimethyl-1-butyne, dimethylamino acetone, propylene oxide, N-ethylmethylamine, bromomethane, N-ethyldimethylamine, methylene chloride, pentane, cyclopentane, 2.3.-pentadiene, cyclopentene, or mixtures thereof.

16. Solid microparticles as in claim 14, with a gas selected from the group consisting of air, nitrogen, oxygen, carbon dioxide, hydrogen, ammonia, ethylene, methane, propane, 17. Solid microparticles which comprise cyclodextrine or cyclodextrine derivatives containing a gas and/or a fluid with a boiling point below 60° C,. wherein the microparticles are of a size within the range of 1–10 μm and are suitable for administration to a subject by injection.

18. An ultrasonic contrast agent according to claim 1, wherein the microparticles are of a size within the range of 1–10 μm.

* * * * *